United States Patent
Saifi et al.

[11] 4,007,631
[45] Feb. 15, 1977

[54] METHOD AND APPARATUS FOR EVALUATING WELDS USING STRESS-WAVE EMISSION TECHNIQUES

[75] Inventors: Mansoor Ali Saifi; Sotirios John Vahaviolos, both of East Windsor Township, Mercer County, N.J.

[73] Assignee: Western Electric Co., Inc., New York, N.Y.

[22] Filed: Aug. 18, 1975

[21] Appl. No.: 605,481

[52] U.S. Cl. .............................. 73/71.4
[51] Int. Cl.² ............................. G01N 29/00
[58] Field of Search .......... 73/67, 71.4, 88.3; 228/103, 104

[56] References Cited
UNITED STATES PATENTS

| | | | |
|---|---|---|---|
| 3,713,127 | 1/1973 | Keledy et al. ................ | 73/67 X |
| 3,782,183 | 1/1974 | O'Connor et al. ............ | 73/67 X |
| 3,822,586 | 7/1974 | Pollock ....................... | 73/71.4 |

OTHER PUBLICATIONS

Jolly "The Application of Acoustic Emission to In--Process Inspection of Welds" in Materials Evaluation vol. 28, No. 6 6/70 pp. 135–139 and 144.

Beattie et al. "The Measurement of Energy in Acoustic Emission " in Rev. Sci. Instruments vol. 45, No. 3 March 74 pp. 352–357.

*Primary Examiner*—Herbert Goldstein
*Attorney, Agent, or Firm*—E. W. Pfeifle; D. J. Kirk

[57] ABSTRACT

Spot welds are evaluated using stress-wave emission techniques by measuring the stress-wave energy emitted from the weld area during $n$ time intervals of the weld cycle, where $n \geq 4$. Each of the time intervals corresponds to a different aspect of the weld cycle such as, for example, the initiation of heating, the separate solid-to-liquid phase transformation in each of the articles being welded, material combination within the weld nugget, cooling stresses occurring during resolidification, and post-weld cracking. The energy values obtained for each of the time interval can be compared with predetermined acceptable energy value ranges for corresponding ones of the intervals and/or compared with predetermined ratio values between two or more of the obtained interval values to determine the quality of a weld.

10 Claims, 4 Drawing Figures

METHOD AND APPARATUS FOR EVALUATING WELDS USING STRESS-WAVE EMISSION TECHNIQUES

BACKGROUND OF THE INVENTION

1. Field of the Invention

This invention relates to method and apparatus for the real-time monitoring of welds using stress-wave emission techniques, and more particularly, to method and apparatus for monitoring welds by measuring the stress waves emitted during $n$ time intervals of the weld cycle, where $n \geq 4$, and comparing the measurements obtained for the intervals with predetermined acceptable ranges for measurements selected from corresponding ones of the intervals and corresponding predetermined ratios between measurements for two or more intervals.

2. Description of the Prior Art

The ability to evaluate a weld using real-time, non-destructive methods has always been of interest to industry. A method for monitoring a welding operation is disclosed in U.S. Pat. No. 3,726,130, issued to R. P. Hurlebaus on Apr. 10, 1973. There, ultrasonic shear wave pulse signals are transmitted into the two pieces to be welded from a transducer positioned opposite the welding electrode while the welding operation is being performed. These signals are reflected from the area between the melting metal and the solid metal to provide real-time data for detecting the degree of penetration of a weld.

Another method for monitoring a welding operation is disclosed in an article entitled, "Forecasting Failures with Acoustic Emissions," by R. E. Herzog published in *Machine Design*, June 14, 1973, at pages 132–137. There it is stated that one of the more successful uses of acoustic emissions is in inspecting welds as they are being made by detecting and correlating signals emitted during the liquid-to-solid phase transformation of a weld area to indicate good or bad welds. The Herzog article further specifies that complex stress waves occur in both the weld cycle and post-weld cooling period, but only emissions during the post-weld cooling period are used for finding defects, such as cracks, as they occur in the weld area, and that emissions during the weld cycle are ignored.

It is also known to detect and measure the stress waves emitted from a weld area during a first solid-to-liquid phase transformation interval and a second liquid-to-solid phase transformation interval and then subtract the stress-wave energy measured during the second transformation interval from the stress-wave energy measured during the first transformation interval to provide an indication of the strength of the weld.

In any welding process, the region of two or more materials in intimate contact are melted and fused. The energy required for melting can be provided either by a current pulse as in resistance or capacitor discharge welding or by a radiation pulse from a laser. For an on-line determination of the quality and the extent of a weld, it is desirable to monitor the real-time evolution of the complete welding process; such as initiation of heating, solid-to-liquid phase transformation, fusion, and resolidification of the weld nugget, since each of these aspects, and others, can affect the quality and/or the extent of a weld. The problem still remains of providing method and apparatus which will evaluate the complete welding process.

BRIEF SUMMARY OF THE INVENTION

The present invention relates to method and apparatus for the real-time monitoring of welds using stress-wave emission techniques, and more particularly, to method and apparatus for monitoring welds by measuring the stress waves emitted during $n$ time intervals of the weld cycle, where $n \geq 4$, and comparing the measurements obtained for the intervals with predetermined acceptable ranges for measurements selected from corresponding ones of the intervals and corresponding predetermined ratios between two or more intervals.

Other and further aspects of the present invention will become apparent during the course of the following description and by reference to the accompanying drawings.

BRIEF DESCRIPTION OF THE DRAWINGS

Referring to the drawings, in which like numerals represent like parts in the several views.

DETAILED DESCRIPTION

The welding process occurs by engaging the articles to be welded together, melting the articles at their common interface, causing material combination or expulsion, and permitting the molten volume to solidify. The required interfacial heat can be supplied in a number of different ways, one of which is by laser welding where a beam of radiation is projected at the articles in the area of the desired weld. The present invention has been described primarily with relation to a laser welding device. However, it will be understood that such description is exemplary only and is for the purpose of exposition and not for purposes of limitation. It will be readily appreciated that the inventive concept is equally applicable for use with any other welding apparatus, such as, for example, a capacitance discharge welder.

Figure 1:
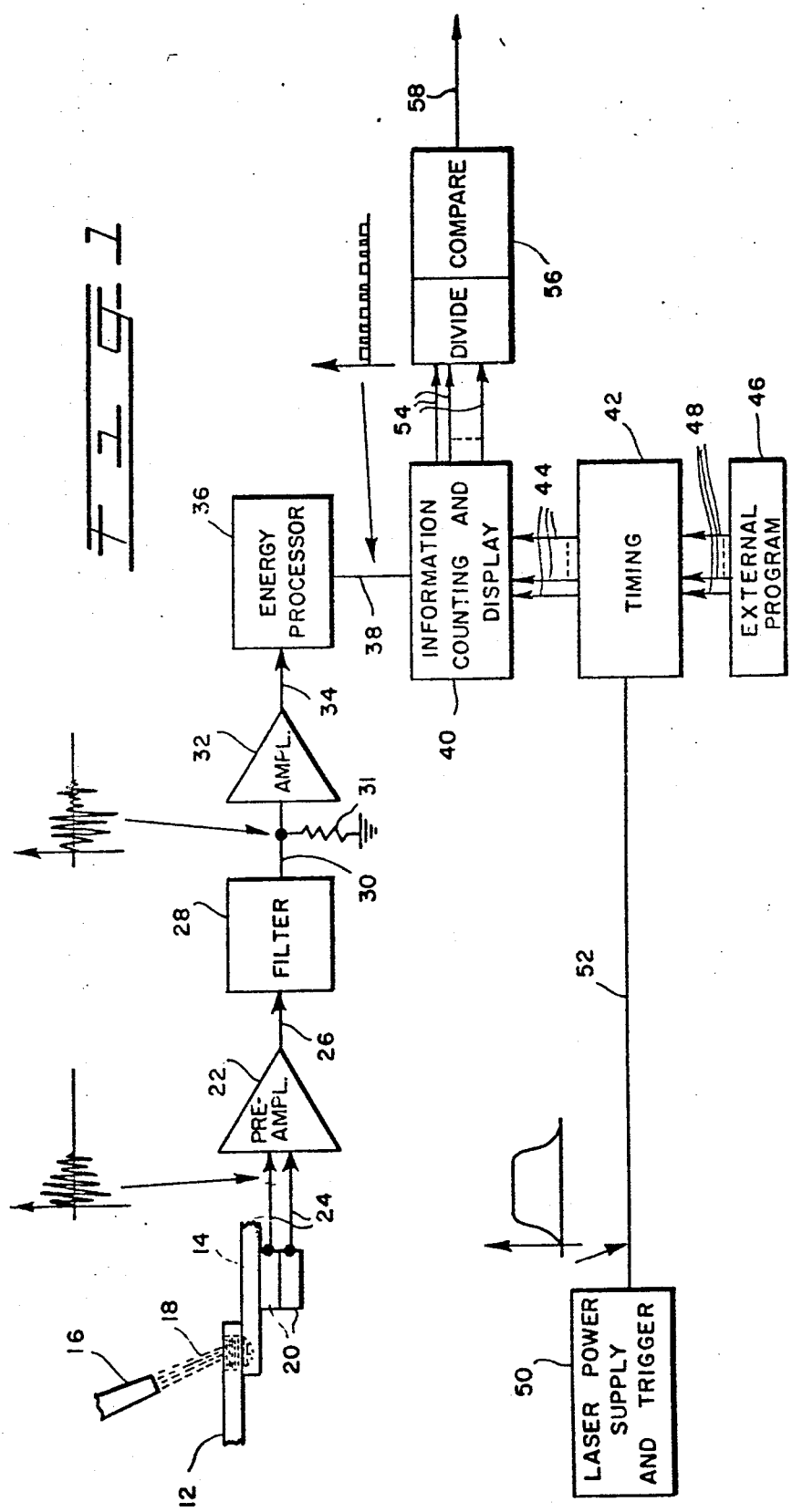
FIG. 1 is a simplified block diagram of a weld-evaluating system according to the present invention.

Referring now to FIG. 1, a pair of overlapping articles 12 and 14, comprising the same or different materials, are positioned to be welded together with a laser beam 18 from a laser 16. Where articles 12 and 14 comprise different materials, the article formed of the higher melting point material is preferably placed nearest laser 16 such that when laser 16 is energized the beam of radiation 18 emitted therefrom advantageously impinges the article having the higher melting point material first. If the laser beam were to impinge the lower melting point material first, the tendency would be for the lower melting point material to vaporize before sufficient heat is transmitted through the lower melting point material to melt the higher melting point material in the weld area. The beam of radiation 18 from laser 16, therefore, should provide only sufficient energy to melt or plastically deform the weld area at the interface of articles 12 and 14 without vaporization or loss of material.

Stress waves are emitted from the weld area during both the weld pulse and post-weld intervals and are detected by a piezoelectric differential transducer 20 (hereinafter referred to as sensor 20) of the present weld evaluation apparatus. Sensor 20 is shown as mechanically coupled to article 14, but could also, for instance, be mechanically coupled to article 12 or, for non-contact detection purposes, to a part of the laser welding apparatus (not shown) which is coupled to either one of articles 12 and 14 and comprises a material having a bulk sonic velocity which closely corresponds to the velocity of sound in the material of articles 12 and 14.

The signals which are detected by sensor 20 comprise mechanical waves which are: (a) generated by other electrical and mechanical components in proximity to the system of FIG. 1, but not shown; (b) generated in articles 12 and 14, or sensor 20 due to nontransient factors such as temperature and strain variations; and (c) stress waves, comprising bulk and surface waves, propagating from the weld area in articles 12 and 14, while the articles are being welded.

During the welding process, energy is released from the weld area in the form of stress waves, which waves, in turn, along with the possible unwanted mechanical waves generated by other electrical and mechanical components and in articles 12 and 14, as indicated above, excite sensor 20. Depending on wave damping at the interfaces, the traveling mechanical stress impulses will cause sensor 20 to provide output voltage changes which are almost proportional to the amplitude of the impulses. Sensor 20, however, should preferably be chosen to have a natural frequency, which can be any frequency as, for example, 1 megahertz, which falls within the frequency range of the emitted stress waves from the weld area but preferably outside the frequency range of the unwanted mechanical waves generated by other sources. In this manner, sensor 20 acts as a filter to generate an electrical output signal primarily representative of the stress waves emitted from the weld area and possibly including a very small component of the substantially attenuated unwanted mechanical waves from other sources. Because of the low amplitude of the stress-wave pulses, it is advantageous to provide for good transmission of the mechanical wave or amplification of the sensor's output voltage.

As shown in FIG. 1, sensor 20 is connected to a low-noise preamplifier 22 by leads 24. Preamplifier 22 should be of a design having a sensitivity which is preferably in the range of 1–4 $\mu$V, but can include a sensitivity beyond this range. In any case, preamplifier 22 should be sufficiently sensitive for the particular application.

The output from preamplifier 22 is transmitted over lead 26 to a band-pass filter 28 which has a pass-band that falls at least partially within the natural frequency of sensor 20, but which falls outside the range of spurious noise frequencies generated by other components in proximity to the system. Filter 28, therefore, functions to only pass the amplified electrical signals from sensor 20 representative of the emitted stress waves from the weld area while simultaneously eliminating any amplified electrical signal from sensor 20 representative of the unwanted mechanical waves from other sources. Filter 28 is preferably a fifth order, or higher, high-pass filter which is commercially available. The output of filter 28 on lead 30 is further amplified by an amplifier 32. A resistor 31 is preferably added to lead 30, as shown, to match the input impedance of amplifier 32. Amplifier 32 is of a design which advantageously has a fast slewing rate, such as, for example, a commercially available model 715 operational amplifier. The output of amplifier 32 is transmitted over lead 34 to an energy processor 36.

Energy processor 36 receives the amplified and filtered signal on lead 34 and encodes the stress-wave signal released from the weld area during both the weld pulse and the post-weld intervals into a digital signal.

Energy processor 36 can comprise circuitry which operates in accordance with a very fast analog-to-digital conversion scheme. Such circuitry, however, is generally very expensive.

Figure 2:
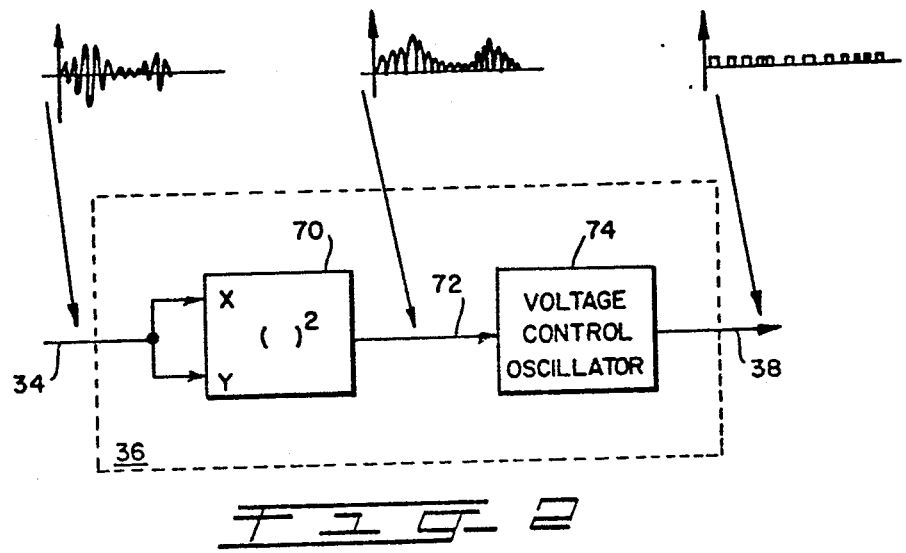
FIG. 2 is a simplified block diagram of an arrangement of the energy processor of FIG. 1.
Figure 3:
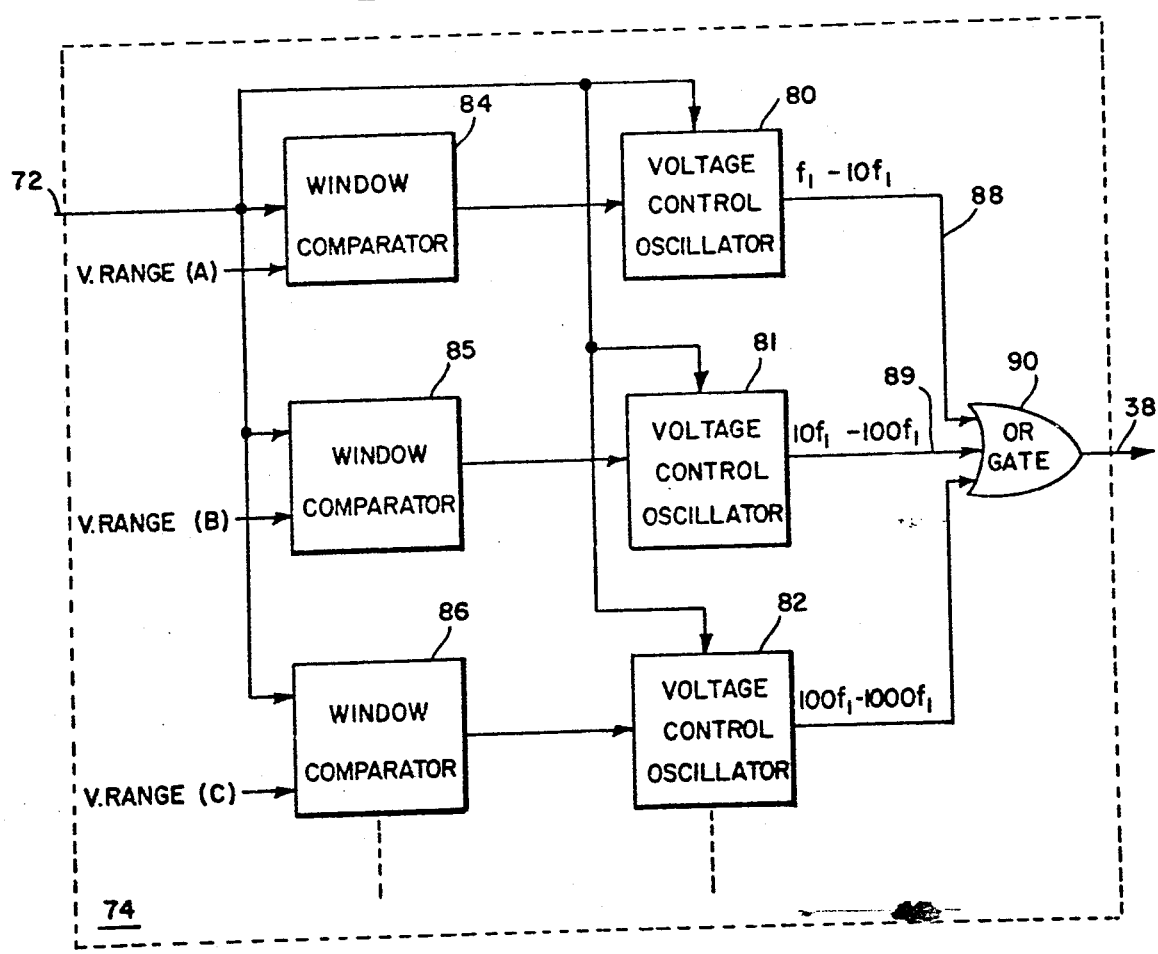
FIG. 3 is a simplified block diagram of a voltage control oscillator for use in the energy processor of FIG. 2.

FIGS. 2 and 3 illustrate an energy processor 36 which comprises very fast yet relatively inexpensive circuitry capable of use in the present weld evaluation system. Energy processor 36 is shown as including a multiplier circuit 70 which provides an output signal on lead 72 that is the square of the input signal on lead 34, and a voltage control oscillator 74. Multiplier 70 can comprise any of a number of circuits such as, for example, a model 4456 multiplier from Teledyne-Philbric of Dedham, Mass. Voltage control oscillator 74 functions to convert the squared amplitude-modulated input signal on lead 72 into a digital frequency-modulated (FM) output signal, a change in the amplitude of the input signal causing a corresponding change in the rate, or frequency, of the digital pulses in the output signal.

Voltage control oscillator 74 should preferably comprise circuitry which provides a frequency range of approximately 1000:1. Since conventional voltage control oscillators generally provide a frequency range of up to 10:1, the novel voltage control oscillator circuitry 74 of FIG. 3 is preferably used in the present system. There, separate, commercially available voltage control oscillators (VCO) 80, 81, and 82 provide a digital FM output signal within the range of $f_1$ to $10f_1$, $10f_1$ to $100f_1$, and $100f_1$ to $1000f_1$, respectively. Frequence $f_1$ can comprise any frequency, as, for example, 1 kilohertz. Each VCO 80, 81, and 82 has a separate respective window comparator 84, 85, and 86 associated therewith. Each window comparator 84, 85, and 86 compares the instantaneous voltage level of the input signal on lead 72 with a different portion of the maximum input signal voltage amplitude range and provides an enable signal to the associated VCO 80–82 when the input voltage level falls within the associated voltage amplitude range A, B, or C under comparison. For example, if the maximum input signal voltage amplitude range is found to be 1.5v, then window comparators 84, 85 and 86 might compare the input voltage level with a voltage amplitude range of 0–0.5v (Range A), 0.5–1.0v (Range B), and 1.0–1.0v (Range C), respectively. The input signal on lead 72 is also supplied to each of the VCOs 80–82.

In operation, if the input signal on lead 72 is assumed to include a voltage level which is rising through the entire ranges of range A and B, then window comparator 84 supplies an enable signal to VCO 80 for as long as the input voltage level is rising within range A. The enable signal from window comparator 84 causes VCO 80 to generate a digital FM output signal on lead 88 which increases in frequency from $f_1$ to $10f_1$ as the input voltage level correspondingly increases through range A. When the input voltage level reaches the lower edge of range B, window comparator 84 causes to generate an enable signal to VCO 80 and window comparator 85 now supplies an enable signal to VCO 81. The enable signal from window comparator 85 causes VCO 81 to generate a digital FM output signal on lead 89 which increases in frequency from $10f_1$ to $100f_1$ as the input voltage level correspondingly increases through range B. The output from each of VCOs 80–82 is coupled to a common OR-gate 90 and onto lead 38 for transmission to an information counting and display circuit 40. Thus, the output signal from voltage control oscillator circuitry 74 can comprise serial pulses ranging in frequency between the frequency $f_1$ and the frequency $1000f_1$ in direct correspondence with voltage amplitude variations in the input signal to VCO circuitry 74 over the maximum input signal amplitude range including ranges A–C. It is, of course, possible to add further window comparators and VCOs in a manner shown in FIG. 3 to extend the range of operation. The voltage control oscillator circuitry 74 advantageously avoids the use of integrators which are generally limited in bandwidth and accuracy.

Figure 4:
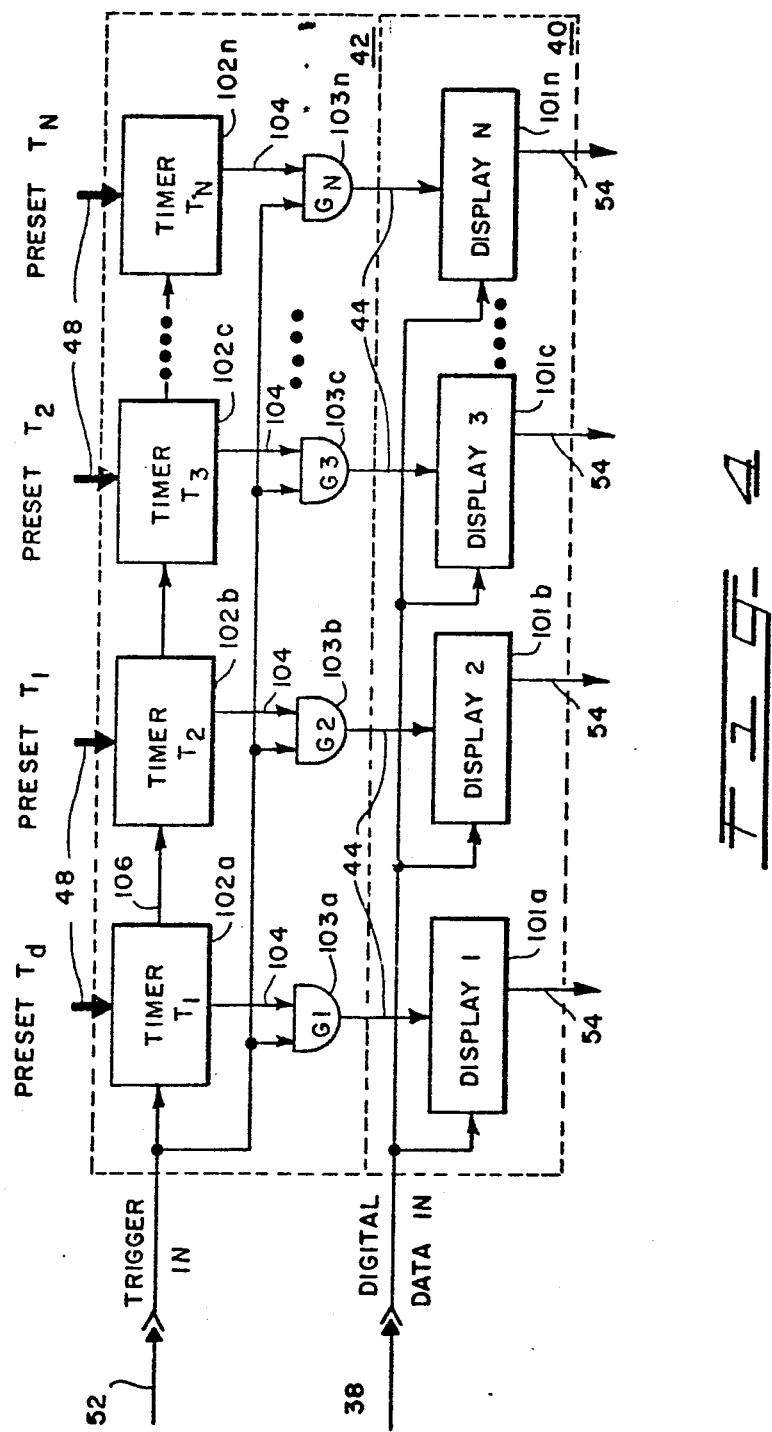
FIG. 4 is a simplified block diagram of an arrangement for the timing and the information counting and display circuit of FIG. 1.

The digital FM output signal from energy processor 36 is transmitted over lead 38 to an information counting and display circuit 40. Information counting and display circuit 40 functions to separately count the input digital pulses relating to each of $n$ predetermined time intervals of the weld cycle, where $n \geq 4$, each time interval corresponding to a different aspect of the weld cycle. Typical aspects of the weld cycle may include, for example, the initiation of heating, the separate solid-to-liquid phase transformation of the material of each of articles 12 and 14 in the weld area, the material combination or expulsion in the weld area after melting, cooling stresses occurring during the resolidification of the weld nugget, and the formation of post-weld cracks. FIG. 4 illustrates a typical configuration for use in information counting and display circuit 40 and timing circuit 42 of FIG. 1.

In FIG. 4, the digital FM signal from energy processor 36 is received on lead 38 and applied to one input of each of counters 101a to 101n, counter 101n being the last counter in a series of $n$ counters. Each of counters 101a–n, once enabled, functions to count the digital pulses received on lead 38 relating to a separate aspect of the weld cycle. Timing circuit 42 provides the necessary enable signals to counters 101a to 101n for properly gating the portion of the digital input signal associated with each aspect of the weld cycle to be measured into the respective counter provided for such aspect. The combination of energy processor 36, shown in FIG. 2, and each of counters 101a–101n function in accordance with the equation:

$$E = \int_0^T v^2(t)dt \qquad (1)$$

within a scale factor to measure the stress-wave energy (E) during a time interval from 0 to T for each of the aspects of the weld cycle to be measured. Multiplier 70 squares the instantaneous waveform on lead 34, voltage control oscillator 74 provides a digital representation of the continuous integration of the squared waveform, and each of counters 101a–n provide a sum of the integration over a particular time period corresponding to the respective aspect of the weld cycle being measured.

Timing circuit 42 can comprise any well-known form and is shown in FIG. 4 as comprising timers 102a to 102n, and gates 103a to 103n. Each of timers 102a to 102n is preset internally, or by connection to an external program 46 over leads 48, to be activated for a particular predetermined time period once enabled, and to supply an output signal during the activated period to one input of the associated one of gates 103a to 103n over lead 104. Timer 102a and a second input of each of gates 103a to 103n are connected to the output of laser power supply and trigger circuit 50 by lead 52. Laser power supply and trigger circuit 50 can comprise any well-known circuit, such as, for example, a photodiode, which functions to both detect when laser 16 is energized, and simultaneously provide a trigger pulse on lead 52 which is continuous over the entire weld cycle. The output of gates 103a to 103n are, in turn, connected to second input counters 101a to 101n, respectively, over leads 44.

For purposes of describing the operation of the present apparatus it will be assumed that, (a) articles 12 and 14 are formed of monel and copper, respectively; (b) it is desired to measure the stress-wave energy emitted from the weld area for the following aspects of the weld cycle:

1. The elastic behavior of the material of article 12 (monel) which provides information with respect to the reflection and absorption of light in the material,
2. The solid-to-liquid phase transformation of the monel of article 12 in the weld area,
3. The solid-to-liquid phase transformation of the copper of article 14 in the weld area,
4. The stress resulting from the mixing of the two molten metals in the weld nugget, also known as material explosion or material expulsion,
5. The liquid-to-solid phase transformation of the weld nugget,
6. Thermal cooling and stressing of the weld area, and
7. The formation of post-weld cracks; and (c) the interval of time within the weld cycle has been predetermined experimentally for each of the above aspects and has been either preset in each of the respective timers 102a to 102n, where $N=7$ (seven timers, one for each aspect above), or programmed into external program 46.

In operation, articles 12 and 14 are overlapped and positioned to be welded together in line with laser 16. Laser 16 is then advantageously energized under conditions which will ensure melting or plastic deformation, but not drilling or vaporization, of the materials of articles 12 and 14 while concurrently controlling the depth of penetration of the weld. In response to laser 16 being energized, laser power supply and trigger circuit 50 generates a trigger pulse which is continuous over the entire weld cycle and is transmitted over lead 52 to timing circuit 42. The impinging of laser beam 18 on the weld area during the weld cycle causes stress waves to be emitted which relate to, but are not necessarily limited to, the various aspects of the weld cycle to be measured. As indicated hereinabove, the emitted stress waves are detected and processed by sensor 20, preamplifier 22, filter 28, amplifier 32, and energy processor 36 to provide a digital signal on lead 38 corresponding to the instantaneous stress-wave energy.

As can be seen from FIG. 4, the trigger pulse on lead 52 is simultaneously applied to one input of both timer 102a and each of the seven gates 103a to 103n, where N=7 (one gate and associated timer for each aspect of the weld cycle to be measured). The digital signal on lead 38 is simultaneously applied to a first input of each of the seven counters 101a to 101n, where n=g (one for each aspect of the weld cycle to be measured). In response to the trigger pulse on lead 52, timer 102a, after a predetermined built-in delay, is energized to provide a continuous enable pulse on lead 104 to gate 103a for a period of time (T1) corresponding to that period where the digitalized signal relating to the stress-wave energy for the first aspect of the weld cycle to be measured arrives at the input to counters 101a to 101g. The combination of a trigger pulse on lead 52 and an enable pulse from timer 102a on lead 104 energizes gate 103a and causes an enable pulse to be transmitted over lead 44 to counter 101a. The enable pulse from gate 103a to counter 101a causes only counter 101a to count the pulses received over lead 38 since counters 101b to 101g are disabled during this period. When timer 102a is disabled, a pulse is transmitted from timer 102a to timer 102b over lead 106 which causes timer 102b to be energized during the time period (T2) corresponding to the period when the digitalized signal relating to the stress-wave energy for the second aspect of the weld cycle is received at the input to counters 101a to 101g. When timer 102b is energized, gate 103b is enabled to provide an enable signal to counter 101b over lead 44, thereby to gate the digital-input signal into counter 101b and measure the stress-wave energy relating to the second aspect of the weld cycle. Timers 102c to 102g, gates 103c to 103g, and counters 101c to 101g are similarly sequentially enabled to provide a window during which the stress-wave energy relating to each particular aspect of the weld cycle to be measured is gated into the associated counter.

After the stress-wave energy emitted from the weld area for each of the seven aspects has been measured and recorded in counters 101a to 101g, the values in each counter can advantageously be visually compared with predetermined acceptable energy value ranges for corresponding ones of the aspects and/or compared with predetermined ratio values between two or more of corresponding aspects, or transmitted over leads 54 to suitable comparing means 56 capable of similarly comparing the recorded values with a predetermined permissible range of energy values for each aspect and/or predetermined corresponding ratios between the measured energy of two or more of the aspects to determine the quality of a particular weld. Ratios can be formed using any well known divider circuit such as AM2LS14 manufactured by the Advanced Microdevices Corporation while the comparison can be made using an SN7485 comparator manufactured by the Texas Instruments Corporation. Typical examples and considerations in this regard may be, for instance, (a) an unacceptable weld might be indicated where a large count is obtained for the elastic behavior aspect (aspect 1, above) indicating that sufficient energy has been absorbed in the weld area to form the weld, and a small count is obtained for the material combination aspect (aspect 4, above), or (b) an acceptable weld may be indicated where a better than average count is obtained relating to the material combination aspect and a small count relating to the post-weld cracking aspect (aspect 7, above) is obtained. Comparing means 56 can also advantageously include circuitry for generating a go-no-go signal on lead 58 to an audible or visual means (not shown) for indicating either an acceptable or an unacceptable weld. For example, a "go" signal can be generated to indicate an acceptable weld when each of the recorded values and/or ratios being compared, for instance, exceed the minimal predetermined permissible values for such values and/or ratios, and a "no-go" signal can be generated indicating an unacceptable weld when one or more of the recorded values and/or ratios being compared fail to, for instance, exceed the minimal predetermined permissible values for such values and/or ratios. It is to be understood that the predetemined acceptable energy value measurement range for each aspect and/or each predetermined ratio value between two or more of the measured aspects, against which corresponding energy value measurements and/or corresponding ratios are to be subsequently compared, can be easily determined. For example, each predetermined energy value measurement range and/or predetermined ratio value can be predetermined by forming a number of sample welds, of the same type to be subsequently tested, under varying conditions of, for instance, input energy to the weld and cleanliness of the articles 12 and 14 at the weld interface while recording the stress-wave-energy value for each aspect. The measured stress-wave-energy values can then be correlated with data obtained during the examination and testing, such as destructive testing, of each sample weld with regard to weld area, weld strength, etc., to determine the predetermined energy value ranges and predetermined ratio values.

It is to be understood that the above-described embodiments are simply illustrative of the principles of the invention. Various other modifications and changes may be made by those skilled in the art which will embody the principles of the invention and fall within the spirit and scope thereof.

What is claimed is:

1. A method for the real-time, non-destructive evaluation of a weld using stress-wave emission techniques, comprising the steps of:
    a. dividing a weld cycle into $n$ intervals of time where $n \geq 4$, each interval corresponding to a different aspect occurring in the weld area during said weld cycles;
    b. measuring stress-wave energy emitted from the weld area during each of said intervals;
    c. forming ratios of the measured stress-wave energies between at least two of said time interval measurements; and
    d. determining the acceptability of a particular weld by comparing the measurements obtained for said $n$ time intervals and the ratios thereof with a set of predetermined acceptable ranges for measurements selected from any combination of corresponding ones of said $n$ time intervals and the corresponding ratio of said interval measurements.

2. A method according to claim 1 comprising the additional step of:
    d. generating an output signal indicative of an acceptable weld when the results of said comparisons indicate that the measurements and ratios thereof being compared exceed the minimum predetermined acceptable value for such measurements and their ratios.

3. A method for the real-time, non-destructive evaluation of a weld being formed between a first and a second article using stress-wave emission techniques, comprising the steps of:

a. detecting the stress waves propagating in the material of said articles and generating an electrical signal representative of said detected waves;
b. amplifying said electrical signal;
c. filtering said amplified electrical signal for generating an analog output signal within a pass band substantially including only said detected stress waves;
d. measuring stress-wave energy during each of $n$ intervals of a weld cycle, where $n \geq 4$, each interval corresponding to a different aspect occurring in the weld area during the weld cycle;
e. forming ratios of the measured stress-wave energies between at least two of said time interval measurements; and
f. determining the acceptability of a particular weld by comparing the measurements obtained for each of said $n$ intervals and the ratios thereof with a set of predetermined acceptable ranges for measurements selected from any combination of corresponding ones of said $n$ time intervals and the corresponding ratios of said time interval measurements.

4. Apparatus for detecting and measuring stress waves propagating from a weld area between first and second articles being welded together for the real-time, non-destructive evaluation of said weld, the apparatus comprising:

a. a sensor for detecting stress waves propagating in the material of said articles and generating an electrical output representative of the detected waves;
b. a first signal-processing means comprising:
   i. an amplifier for amplifying the electrical output from said sensor; and
   ii. a band-pass filter connected to the output of said amplifier for generating an analog output signal within a pass band falling outside the range of frequencies normally generated by components in proximity to the apparatus;
c. second signal-processing means connected to the output of said first signal-processing means for measuring the stress-wave energy in each of $n$ time intervals of a weld cycle, where $n \geq 4$, each interval corresponding to a different aspect occuring in the weld area during the weld cycle;
d. means for comparing measurements selected from any combination of stress-wave energy represented in corresponding ones of said $n$ time intervals and the corresponding ratios between at least two of said time interval measurements to predetermined acceptable ranges to determine the acceptability of the weld.

5. Apparatus according to claim 4 wherein said second signal-processing means comprises:
   i. encoding means, connected to the output of said first signal-processing means, for generating a digital signal indicative of the energy of the output signal of said first signal-processing means; and
   ii. means for separately counting the digital pulses from said encoding means during each of said $n$ time intervals.

6. Apparatus according to claim 5 wherein said encoding means comprises:
   a multiplier circuit for squaring the output signal from said first signal-processing means, and
   voltage control oscillator circuitry connected to said multiplier circuit for generating a digital frequency-modulated signal indicative of the energy of said squared signal from said multiplier circuit.

7. Apparatus according to claim 5 wherein said means for separately counting the digital pulses comprises:
   a plurality of $n$ counters, one for each of said $n$ time intervals; and
   timing means for gating the digital signal from said encoding means associated with each of said $n$ time intervals into the corresponding one of said plurality of $n$ counters.

8. Apparatus according to claim 4 wherein said second signal-processing means comprises:
   means for comparing the measurements from any combination of selected ones of said $n$ time intervals and the ratio between at least two of said time intervals with predetermined acceptable ranges for such measurements and their ratios, and generating an output signal indicative of an acceptable weld when each of said compared measurements and ratios exceeds the minimum predetermined acceptable value for such measurements and their ratios.

9. Apparatus for detecting and measuring stress waves propagating from a weld area between first and second articles being welded together, for the real-time, non-destructive evaluation of said weld, the apparatus comprising:
   a. a sensor for detecting stress waves propagating in the material of said artic... to ...duce an electrical output representative of the detected waves;
   b. first signal-processing means comprising:
      i. an amplifier for am... the electrical output from said sensor, and
      ii. a band-pass filter connected to the output of said amplifier for generating an analog output signal within a pass-band falling outside the range of frequencies normally generated by components in proximity to the apparatus; and
   c. second signal-processing means comprising:
      i. encoding means, connected to the output of said first signal-processing means, for generating a digital signal indicative of the stress-wave energy in the output signal of said first signal-processing means;
      ii. means connected to the output of said encoding means for searately measuring the stress-wave energy in each of $n$ time intervals of a weld cycle where $n \geq 4$, each time interval corresponding to a different aspect occurring in the weld area during the weld cycle; and
      iii. means for comparing the measurements from any combination of selected one of said $n$ time intervals and the ratio between at least two of said time interval measurements with predetermined acceptable ranges for such measurements and their ratios.

10. Apparatus according to claim 9 wherein said second signal-processing comparing means further comprises:
    means for generating an output signal indicative of a acceptable weld when each of said compared measurements and ratios exceeds the minimum predetermined acceptable value for such measurements and their ratios.

* * * * *